US010717698B2

(12) United States Patent
Mohammadi et al.

(10) Patent No.: US 10,717,698 B2
(45) Date of Patent: Jul. 21, 2020

(54) RESVERATROL GLYCOLATE AND TARTRATE DERIVATIVES AND SYNTHETIC METHODS THEREFOR

(71) Applicant: ELC MANAGEMENT LLC, Melville, NY (US)

(72) Inventors: Fatemeh Mohammadi, Hauppauge, NY (US); Elham Tavasoli, Farmingdale, NY (US)

(73) Assignee: ELC Management LLC, Melville, NY (US)

( * ) Notice: Subject to any disclaimer, the term of this patent is extended or adjusted under 35 U.S.C. 154(b) by 0 days.

(21) Appl. No.: 16/081,842

(22) PCT Filed: Mar. 6, 2017

(86) PCT No.: PCT/US2017/020923
§ 371 (c)(1),
(2) Date: Aug. 31, 2018

(87) PCT Pub. No.: WO2017/155875
PCT Pub. Date: Sep. 14, 2017

(65) Prior Publication Data
US 2019/0071386 A1    Mar. 7, 2019

Related U.S. Application Data

(60) Provisional application No. 62/304,541, filed on Mar. 7, 2016.

(51) Int. Cl.
| *C07C 67/317* | (2006.01) |
| *C07C 69/675* | (2006.01) |
| *C07C 67/14* | (2006.01) |
| *A61K 8/37* | (2006.01) |
| *A61Q 19/08* | (2006.01) |
| *A61Q 19/00* | (2006.01) |
| *C09B 23/14* | (2006.01) |
| *C07B 51/00* | (2006.01) |

(52) U.S. Cl.
CPC ............ *C07C 67/317* (2013.01); *A61K 8/375* (2013.01); *A61Q 19/00* (2013.01); *C07C 67/14* (2013.01); *C07C 69/675* (2013.01); *C09B 23/148* (2013.01); *A61K 8/37* (2013.01); *A61Q 19/08* (2013.01); *C07B 51/00* (2013.01)

(58) Field of Classification Search
CPC ...... C07C 67/317; C07C 67/14; C07C 69/675; A61K 8/375; C09B 23/148
See application file for complete search history.

(56) References Cited

U.S. PATENT DOCUMENTS

| 9,220,669 B2 | 12/2015 | Bratescu et al. |
| 2006/0173065 A1 | 8/2006 | Bezwada |
| 2008/0139650 A1 | 6/2008 | Jakob et al. |
| 2009/0215881 A1 | 8/2009 | Delaire et al. |
| 2017/0210694 A1* | 7/2017 | Boo et al. ............ A61K 8/37 |

FOREIGN PATENT DOCUMENTS

| KR | 20050011174 | 1/2005 |
| KR | 20140094394 | 7/2014 |
| KR | 101735996 | 5/2017 |
| WO | WO-2009/017866 | 2/2009 |
| WO | WO-2009/023416 | 2/2009 |
| WO | WO-2009/032896 | 3/2009 |
| WO | WO-2013/008194 | 1/2013 |
| WO | WO-2016/011319 A1 | 1/2016 |

OTHER PUBLICATIONS

PCT International Search Report; International Application No. PCT/US2017/020923; Completion Date: Jun. 13, 2017; dated Jun. 13, 2017.
PCT Written Opinion of the International Searching Authority; International Application No. PCT/US2017/020923; Completion Date: Jun. 13, 2017; dated Jun. 13, 2017.
Beutel, et al.; Resolution of Racemic [alpha]-Hydroxyy-[beta],[beta]-dimethyl-[gamma]-butyrolactone; Journal of The American Chemical Society; vol. 68; No. 8; pp. 1463-1465; Aug. 1946.
Kam, et al.; [(Arylcarbonyl)oxy]propanolamines. 1. Novel .beta.-Blockers with Ultrashort Duration of Action; Journal of Medicinal Chenmistry; vol. 27; No. 8; pp. 1007-1016; Au.
Kim, et at.; Supporting Information—Multivalent Nanofibers of a Controlled Lenght: Regulation of Bacterial Cell Agglutination; Journal of the American Chemical Society; pp. S1 -S16; Sep. 2012.
Supplementary European Search Report; EP Application No. 17763831.9; Completion Date: Jun. 19, 2019; dated Jul. 11, 2019.

* cited by examiner

*Primary Examiner* — Paul A Zucker
(74) *Attorney, Agent, or Firm* — Julie M. Blackburn; Sonsy P. Rajan; Yonggang Wu

(57) ABSTRACT

The present invention relates to compounds of ester derivative of resveratrol, compositions comprising ester derivatives of resveratrol, processes for synthesizing an ester of resveratrol, and use thereof.

14 Claims, No Drawings

RESVERATROL GLYCOLATE AND TARTRATE DERIVATIVES AND SYNTHETIC METHODS THEREFOR

TECHNICAL FIELD

The invention is in the field of resveratrol derivative compounds and compositions, and methods for synthesizing same.

BACKGROUND OF THE INVENTION

Resveratrol, also referred to as 3,5,4'-trihydroxystilbene, is a polyhydroxy-substituted compound having the general formula:

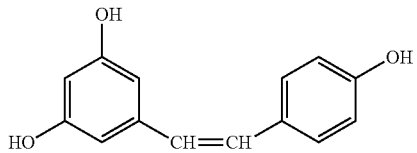

It is present in red grapes, raspberries, blueberries, and certain other plant berries or extracts. It is known that resveratrol is a potent anti-oxidant and has other anti-aging, anti-cancer, and antiviral effects. Because of its perceived fountain-of-youth properties, resveratrol has been incorporated into a variety of cosmetic formulations, such as skin creams. However, because resveratrol is somewhat unstable it readily discolors. In addition, it is most desirable to react resveratrol with other compounds to create resveratrol derivatives in order to maximize its effectiveness for properties such as stability, activity, and beneficial effects on skin.

Alpha hydroxy acids or AHA's are known for their effectiveness in treating skin. The carboxylic acid groups on the compounds aid in skin exfoliation to remove dead skin cells and debris from skin surfaces. It is also said that AHA's reduce the appearance of age-related skin changes such as lines, wrinkles, age spots, mottling, yellowing, and skin laxity. However, AHA's can also cause skin irritation, redness, or dryness in individuals with overly sensitive skin.

Particularly effective AHAs are glycolic and tartaric acids. Glycolic acid has the following formula:

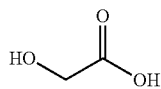

And tartaric acid the following formula:

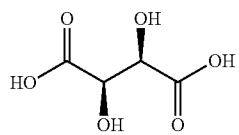

Esterifying resveratrol with glycolic or tartaric acids provides a resveratrol derivative that may be a mono-, di-, or tri-substituted ester on the hydroxyl group to form resveratrol mono-, di- or triglycolate or mixtures thereof, or resveratrol mono-, di-, or tritartrate or mixtures thereof, respectively. Such derivatives can be incorporated into cosmetic compositions to provide beneficial effects such as stimulating collagen or fibrillin synthesis, exfoliating skin, whitening skin, treating acne or other skin lesions, and inhibiting matrix metalloproteinases that degrade collagen.

SUMMARY OF THE INVENTION

The invention is directed to a compound of the formula:

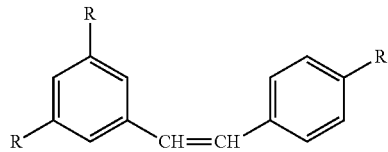

wherein each R is independently selected from:

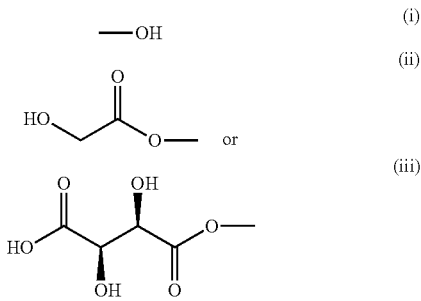

with the proviso that all three R cannot simultaneously be —OH.

The invention is also directed to a method for synthesizing an ester of resveratrol and glycolic acid by:
a) reacting glycolic acid with dihyropyran to yield tetrahydropyran protected glycolic acid,
b) reacting the protected glycolic acid with resveratrol,
c) deprotecting the protected glycolic acid by reacting with acetonitrile; and
d) optionally, purifying the reaction product of (c) by eluting on a column.

The invention is also directed to a method for synthesizing an ester of resveratrol and glycolic acid by:
a) deprotonating resveratrol by reacting with a base,
b) preparing alpha hydroxyl protected glycolic acid by:
  (i) reacting the alpha hydroxyl group of glycolic acid with compound having a protecting donor group to form a protected alpha hydroxy glycolic acid
  (ii) reacting (i) with halogen donor compound to form a reactive alpha hydroxyl acyl halide,
c) reacting (a) and (b) to form alpha hydroxyl protected resveratrol glycolate; and
d) deprotecting the protected alpha hydroxyl groups to form resveratrol glycolate.

The invention is also directed to a method for synthesizing resveratrol tartrate comprising the steps of:
(a) deprotonating resveratrol by reacting with a base,
(b) preparing alpha hydroxyl protected tartaric acid anhydride by:
  (i) dehydrating tartaric acid to form a reactive tartaric acid anhydride,
  (ii) simultaneously reacting the alpha hydroxyl groups with a compound having a protecting donor group to form a protected tartaric acid anhydride, (c) reacting (a) and (b) to form alpha hydroxyl protected resveratrol tartrate; and
(d) deprotecting the protected alpha hydroxyl groups to form resveratrol tartrate.

The invention is also directed to a topical composition comprising a compound of the formula:

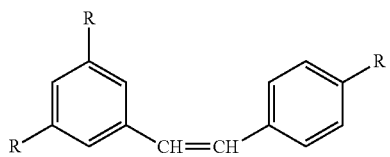

wherein each R is independently selected from:

(i) —OH (ii) 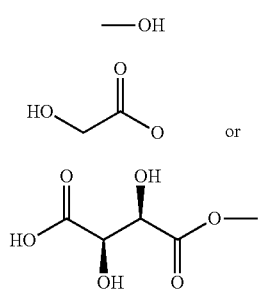 or (iii)

with the proviso that all three R cannot simultaneously be —OH.

DETAILED DESCRIPTION

Resveratrol Glycolate

The ester of resveratrol and glycolic acid may be made as follows:
a) reacting glycolic acid with dihyropyran to yield tetrahydropyran protected glycolic acid,
b) reacting the protected glycolic acid with resveratrol,
c) deprotecting the protected glycolic acid by reacting with acetonitrile; and
d) optionally, purifying the reaction product of (c) by eluting on a column.

The ester of resveratrol and glycolic acid may also be made as follows:
a) deprotonating resveratrol by reacting with a base,
b) preparing alpha hydroxyl protected glycolic acid by:
   (i) reacting the alpha hydroxyl group of glycolic acid with compound having a protecting donor group to form a protected alpha hydroxy glycolic acid
   (ii) reacting (i) with halogen donor compound to form a reactive alpha hydroxyl acyl halide,
c) reacting (a) and (b) to form alpha hydroxyl protected resveratrol glycolate; and
d) deprotecting the protected alpha hydroxyl groups to form resveratrol glycolate.

A suitable base for deprotonating resveratrol includes alkali or alkaline earth metal hydrides such as sodium, potassium, magnesium, lithium and so on. Preferably about 0.5 to 2 mole, most preferably 1 mole of resveratrol is reacted with from about 2 to 10 moles of metal hydride, preferably sodium hydride. In addition the reaction conditions are in the presence of anhydrous argon gas and tetrahydrofuran at room temperature (25° C.). The reaction conditions may range from 1 to 10 hours, most preferably 2 to 6 hours, and will yield deprotonated resveratrol where all three hydrogens are removed from the three hydroxyl groups of resveratrol.

Separately, glycolic acid is reacted with compound having a protecting donor group. Most preferred are pyran compounds which are heterocyclic non-aromatic rings, and in particular mono-, di-, tri-, or tetrahydropyrans (where the mono-, di-, tri- and tetra-refer to the number of hydrogen atoms removed from the pyran ring) and a short chain mono-, di-, or trialkyl halogen where the alkyl is a short chain alkyl such as methyl, ethyl, propyl, and the halogen is chlorine, fluorine, bromine, etc. Most preferred is dimethyl chloride. The reaction may take place in the presence of pyridine, p-Toluenesulfonic acid, and is preferably at room temperature for a period of time ranging from 3-12 hours. More preferred is where the compound having a protecting donor group is dihydropyran, and the alkyl halide is a dimethyl halogen, and in particular dimethyl chloride. About 1.5 moles of dihydropyran is reacted with 1 mole of glycolic acid to yield the alpha hydroxyl glycolate protected with tetrahydropyran. Thereafter the reaction is continued in the presence of $SOCl_2$, dimethyl formamide, and dimethyl chloride under reflux conditions for 4 to 6 hours to yield glycolic acyl chloride where the alpha hydroxyl group is protected with tetrahydropyran. The final step is deprotecting the protected alpha hydroxyl acyl.

Alternatively, after deprotonating the glycolic acid, the hydroxyl group may be protected by reacting with trityl halogens such as trityl chloride (triphenyl methyl chloride) where the alpha hydroxyl group is substituted with triphenyl methyl group. Thereafter the protected compound is reacted with $SOCl_2$, dimethyl formamide, and dimethylchloride under reflux conditions for about 4-6 hours to yield a compound with the trityl protected alpha hydroxyl chloride group. Then, the trityl protected acyl halide form of the compound is reacted with the deprotonated resveratrol to form resveratrol glycolate where the alpha hydroxyl groups on the glycolic acid remain protected with the trityl group. The trityl protecting groups are removed by reaction with one or more of trifluoroacetic acid, ethanediol, dimethylsulfide and dimethylchloride to form resveratrol glycolate.

Another alternative is to purchase a commercially available 2-hydroxy acetyl chloride and react with the deprotonated resveratrol to form resveratrol glycolate. This reaction takes place in the presence of one or more of triethylamine and tetrahydrofuran at room temperature from 12 to 72 hours. The end result is resveratrol glycolate. Depending on the reaction conditions used and the reactant concentrations the resveratrol glycolate may be mono-, di-, or trisubstituted with glycolic acid or in the form of mixtures of the mono-, di-, or trisubstituted esters. In this case the different compounds include 3-glycolate-5-4'-dihydroxystilbene; 5-glycolate-3,4'dihydroxystilbene; 4'-glycolate-3,5-dihydroxystilbene; 3,5-diglycolate-4'-hydroxystilbene; 3,4'-diglycolate-5-hydroxystilbene; 3,4'-diglycolate-5-hydroxystilbene; 4'5-diglycolate-3-hydroxystilbene; and 3,5,4'-triglycolate stilbene.

Resveratrol Tartrate

The tartrate ester of resveratrol may be synthesized by first deprotonating resveratrol as noted above in synthesis of resveratrol glycolate and under same reaction conditions. Separately, tartaric acid is reacted in the presence of acetic anhydride, acetic acid, or pyridine at room temperature for 12-48 hours to yield the acetyl protected tartaric anhydride, O,O'-diacetyl-L-tartaric anhydride. Alternatively, this compound can be purchased commercially.

Thereafter, 1 mole of the deprotonated resveratrol is reacted with 3 moles of the O,O'-diacetyl-L-tartaric anhydride to form the acetyl protected resveratrol tartrate. The protecting groups are removed by reacting with potassium carbonate (10 mole) and methanol at room temperature for 1-6 hours to yield resveratrol tartrate. Depending on the reaction conditions and the amount of reactants used, the resveratrol may be mono-, di-, or tri-substituted with tartaric acid or may be in the form of mixtures of the mono-, di-, and tri-substituted tartaric acid substituted resveratrol. In this case the different compounds include 3-tartrate-5-4'-dihydroxystilbene; 5-tartrate-3,4'dihydroxystilbene; 4'-tartrate-3,5-dihydroxystilbene; 3,5-ditartrate-4'-hydroxystilbene; 3,4'-ditartrate-5-hydroxystilbene; 3,4'-ditartrate-5-hydroxystilbene; 4'5-ditartrate-3-hydroxystilbene; and 3,5,4'-tritartrate stilbene.

Cosmetic Compositions

The resveratrol esters may be incorporated into topical cosmetic compositions that may be in the form of creams, lotions, serums, solutions, dispersions and the like. The compositions may be in the formula of emulsions—either water-in-oil or oil-in-water. Suitable emulsions contain from about 1 to 90% water and 10-90% of other ingredients including oil. Such additional ingredients include, but are not limited to the following.

Oils

Suitable oils include silicones, esters, vegetable oils, synthetic oils, including but not limited to those set forth herein. The oils may be volatile or nonvolatile, and are preferably in the form of a pourable liquid at room temperature. If present, the oils may range from about 0.5 to 85%, preferably from about 1-75%, more preferably from about 5-65% by weight of the total composition.

Cyclic and linear volatile silicones are available from various commercial sources including Dow Corning Corporation and General Electric. The Dow Corning linear volatile silicones are sold under the trade names Dow Corning 244, 245, 344, and 200 fluids. These fluids include hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst) and mixtures thereof, with all viscosity measurements being at 25° C.

Suitable branched volatile silicones include alkyl trimethicones such as methyl trimethicone, a branched volatile silicone having the general formula:

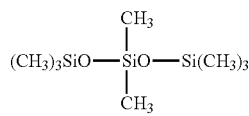

Methyl trimethicone purchased from Shin-Etsu Silicones under the trade name TMF-1.5, having a viscosity of 1.5 centistokes at 25° C.

Also suitable are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

Also suitable are esters formed by the reaction of a carboxylic acid and an alcohol. The alcohol and the carboxylic acids may both have fatty (C6-30) chains. Examples include hexyl laurate, butyl isostearate, hexadecyl isostearate, cetyl palmitate, isostearyl neopentanoate, stearyl heptanoate, isostearyl isononanoate, stearyl lactate, stearyl octanoate, stearyl stearate, isononyl isononanoate, and so on.

The ester may also be in the dimer or trimer form. Examples of such esters include diisotearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

Examples of other types of esters include those from arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, camelina sativa oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diiosostearate, polyglyceryl-3 isostearate, polyglyceryl-4 isostearate, polyglyceryl-6 ricinoleate, glyceryl dioleate, glyceryl diisotearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

Nonvolatile silicone oils, both water soluble and water insoluble, are also suitable for use in the composition. Such silicones preferably have a viscosity ranging from about greater than 5 to 800,000 cst, preferably 20 to 200,000 cst at 25° C. Suitable water insoluble silicones include amine functional silicones such as amodimethicone. Examples include dimethicone, phenyl dimethicone, diphenyl dimethicone, phenyl trimethicone, or trimethylsiloxyphenyl dimethicone. Other examples include alkyl dimethicones such as cetyl dimethicone, stearyl dimethcone, behenyl dimethicone, and the like.

Surfactants

The composition may contain one or more surfactants, especially if in the emulsion form. However, such surfactants may be used if the compositions are anhydrous also, and will assist in dispersing ingredients that have polarity, for example pigments. Such surfactants may be silicone or organic based. The surfactants will aid in the formation of stable emulsions of either the water-in-oil or oil-in-water form. If present, the surfactant may range from about 0.001 to 30%, preferably from about 0.005 to 25%, more preferably from about 0.1 to 20% by weight of the total composition.

Silicone surfactants may be generically referred to as dimethicone copolyol or alkyl dimethicone copolyol. In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or an ether such as methyl ether, ethyl ether, propyl ether, butyl ether, and the like.

Examples of silicone surfactants are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

Also suitable are various types of crosslinked silicone surfactants that are often referred to as emulsifying elastomers that contain at least one hydrophilic moiety such as polyoxyalkylenated groups. Polyoxyalkylenated silicone elastomers that may be used in at least one embodiment of the invention include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers like those disclosed in PCT/WO 2004/024798, which is hereby incorporated by reference in its entirety. Such elastomers include Shin-Etsu's KSG series, such as KSG-710 which is dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

The composition may comprise one or more nonionic organic surfactants. Suitable nonionic surfactants include alkoxylated alcohols, or ethers, formed by the reaction of an alcohol with an alkylene oxide, usually ethylene or propylene oxide. Preferably the alcohol is either a fatty alcohol having 6 to 30 carbon atoms. Examples of such ingredients include Steareth 2-100, which is formed by the reaction of stearyl alcohol and ethylene oxide and the number of ethylene oxide units ranges from 2 to 100; Beheneth 5-30 which is formed by the reaction of behenyl alcohol and ethylene oxide where the number of repeating ethylene oxide units is 5 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, and so on. All recitations of units include all whole integers between the range.

Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol. Examples include polymeric alkylene glycols reacted with glyceryl fatty acid esters such as PEG glyceryl oleates, PEG glyceryl stearate; or PEG polyhydroxyalkanotes such as PEG dipolyhydroxystearate wherein the number of repeating ethylene glycol units ranges from 3 to 1000.

Other suitable nonionic surfactants include alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkyoxylated sorbitan can be esterified with C6-30, preferably C12-22 fatty acids. Examples of such ingredients include Polysorbates 20-85, sorbitan oleate, sorbitan sesquioleate, sorbitan palmitate, sorbitan sesquiisostearate, sorbitan stearate, and so on.

Humectants

It may also be desirable to include one or more humectants in the composition. If present, such humectants may range from about 0.001 to 25%, preferably from about 0.005 to 20%, more preferably from about 0.1 to 15% by weight of the total composition. Examples of suitable humectants include glycols, sugars, and the like. Suitable glycols are in monomeric or polymeric form and include polyethylene and polypropylene glycols such as PEG 4-200, which are polyethylene glycols having from 4 to 200 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on. Also suitable is urea. Preferably, the humectants used in the composition of the invention are $C_{1-6}$, preferably $C_{2-4}$ alkylene glycols, most particularly butylene glycol.

Botanical Extracts

It may be desirable to include one or more botanical extracts in the compositions. If so, suggested ranges are from about 0.0001 to 10%, preferably about 0.0005 to 8%, more preferably about 0.001 to 5% by weight of the total composition. Suitable botanical extracts include extracts from plants (herbs, roots, flowers, fruits, seeds) such as flowers, fruits, vegetables, and so on, including yeast ferment extract, *Padina Pavonica* extract, thermus thermophilis ferment extract, camelina *sativa* seed oil, boswellia serrata extract, olive extract, *Aribodopsis Thaliana* extract,

*Acacia Dealbata* extract, *Acer Saccharinum* (sugar maple), acidopholus, acorns, aesculus, agaricus, agave, agrimonia, algae, aloe, citrus, brassica, cinnamon, orange, apple, blueberry, cranberry, peach, pear, lemon, lime, pea, seaweed, caffeine, green tea, chamomile, willowbark, mulberry, poppy, and those set forth on pages 1646 through 1660 of the CTFA Cosmetic Ingredient Handbook, Eighth Edition, Volume 2. Further specific examples include, but are not limited to, *Glycyrrhiza glabra, Salix nigra, Macrocycstis pyrifera, Pyrus malus, Saxifraga sarmentosa, Vitis vinifera, Morus nigra, Scutellaria baicalensis, Anthemis nobilis, Salvia sclarea, Rosmarinus officianalis, Citrus medica limonum, Panax ginseng, Siegesbeckia orientalis, Fructus mume, Ascophyllum nodosum, Bifida Ferment lysate, Glycine soja* extract, *Beta vulgaris, Haberlea rhodopensis, Polygonum cuspidatum, Citrus aurantium dulcis, Vitis vinifera, Selaginella tamariscina, Humulus lupulus, Citrus reticulata* Peel, *Punica granatum, Asparagopsis armata, Curcuma longa, Menyanthes trifoliata, Helianthus annuus, Hordeum vulgare, Cucumis sativus, Evernia prunastri, Evernia fuifuracea*, and mixtures thereof.

Particulate Materials

The compositions of the invention may contain particulate materials in the form of pigments, inert particulates, or mixtures thereof. If present, suggested ranges are from about 0.01-75%, preferably about 0.5-70%, more preferably about 0.1-65% by weight of the total composition. In the case where the composition may comprise mixtures of pigments and powders, suitable ranges include about 0.01-75% pigment and 0.1-75% powder, such weights by weight of the total composition.

The particulate matter may be colored or non-colored powders. Suitable non-pigmented powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone, or various other agents either alone or in combination, which coat the powder surface and render the particles more lipophilic in nature.

Suitable pigments are organic or inorganic. Organic pigments are generally various aromatic types including azo, indigoid, triphenylmethane, anthroquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof. Iron oxides of red, blue, yellow, brown, black, and mixtures thereof are suitable.

Vitamins and Antioxidants

The compositions of the invention may contain vitamins and/or coenzymes, as well as antioxidants. If so, 0.001-10%, preferably 0.01-8%, more preferably 0.05-5% by weight of the total composition is suggested. Suitable vitamins include ascorbic acid and derivatives thereof such as ascorbyl palmitate, tetrahexydecyl ascorbate, and so on; the B vitamins such as thiamine, riboflavin, pyridoxin, and so on, as well as coenzymes such as thiamine pyrophoshate, flavin adenin dinucleotide, folic acid, pyridoxal phosphate, tetrahydrofolic acid, and so on. Also Vitamin A and derivatives thereof are suitable. Examples are retinyl palmitate, retinol, retinoic acid, as well as Vitamin A in the form of beta carotene. Also suitable is Vitamin E and derivatives thereof such as Vitamin E acetate, nicotinate, or other esters thereof. In addition, Vitamins D and K are suitable.

The invention further comprises treating skin to stimulate collagen synthesis by topically applying a composition tri- or tetrapeptide, at least one penta- or hexapeptide, at least one extract from the *Laminaria* genus, and whey protein. The compositions may be applied in the forms mentioned herein, as part of skin care regimens. For example, the composition may be applied to the skin as a night cream or cream applied to skin prior to a period of bodily rest such as a nap or sleep. The composition may be applied two times a day, in the morning and in the evening after cleansing the skin. The composition may be applied to the skin over skin care products, in the form of foundations or other color cosmetics.

The invention will be further described in connection with the following examples which are set forth for the purposes of illustration only.

Example 1

Resveratrol glycolate was synthesized by first protecting glycolic acid with 3,4-Dihydro-2H-pyran (DHP). DHP, 13.395 grams (159.24 mM), was combined with 4.01 grams (52.73 mM) of glycolic acid in a scintillation vial and heated to 65° C. After the glycolic acid was fully dissolved, 37% HCl, 0.0236 grams (0.24 mM) was added. The temperature was reduced to 45° C. and the vial containing the mixture was maintained in the bath for 60 minutes. The vial was then transferred to an evaporation flask and the excess DHP evaporation for 2 hours at a bath temperature of 45° C., condenser set at 3° C. and vacuum at 300→10 mbar. The bath temperature was then reduced to 25° C. and the vacuum maintained at 10 mbar overnight. The process yielded 12.53 grams of tetrahydropyran (THP) protected glycolic acid.

Then 1.23 grams of resveratrol was mixed with 30 grams of acetonitrile (AcN). The mixture was heated to 45° C. for 1 hour with sonication. Then 2.61 grams of EDC (Ethylene Dichloride) was added and mixed. The THP glycolic acid, 12.53 grams, was added to the mixture. The solution clarified and turned yellow. Solution was closed and allowed to stand overnight at 25° C. The solution showed moderate darkening.

Deprotection of the resveratrol-THP-glycolic acid reaction mixture was accomplished by combining 55 ml of the reaction mixture with 55 ml Acetyl nitrile (Ac N), and 55 ml DI water and mixing with a stir bar. The pH was measured using pH paper to confirm a pH of about 11. HCl, 3.0Normal, 8 ml was added to the mixture with a transfer pipette. The resulting solution lightened and was clear. The sample was concentrated by rotary evaporation until distillation was no longer observed. Yield was 28.07 grams.

The sample was then prepared for loading on a column to remove ACN and water to avoid interference with elution. The concentrated sample was poured into flask containing 50 ml ethyl acetate after it had been rinsed three times with about 15 ml ethyl acetate. The sample was extracted three times with 50 ml aliquots of DI water. The water layers were removed and discarded. The ethyl acetate layer was gravity filtered through a Whatman 1 with about 5 grams of sodium sulfate and rinsed with about 15 ml ethyl acetate. The ethyl acetate was transferred to a 100 ml evaporation flask and evaporated until distillation was no longer observed, with vacuum at 300-10 mbar, bath temperature 45° C. and condenser set at 3° C. This yielded 4.51 grams of sample.

The separation was accomplished by mixing 21 grams of 60 Å pore size 100-200 mesh silica with sufficient 1:1 ethyl acetate:hexane to prepare 2 cm× about 20 cm column. The column was rinsed with 100 ml 1:1 hexanes/ethyl acetate upon settling. The sample was loaded into the column, which was then eluted with 100 ml 1:1 hexanes/ethyl acetate. The eluate was collected (fraction 1). The column was then eluted again with 100 ml ethyl acetate. The eluate was collected as fraction 2. Both fractions were evaporated to dryness. Fraction 1 yielded 116.31 grams; Fraction 2, 113.87 grams. The purification by column chromatography was then performed. The crude form was a blend of mono-, di-, and tri-resveratrol glycolate, unreacted starting material and side products. When column was eluted by 100 mL 1:1 hexanes:ethylacetate fraction 1 was collected containing a significant portion of resveratrol as unreacted material. A small percentage of mono and di-resveratrol glycolate also came out along with unreacted resveratrol as fraction 1. Then column was eluted by 100 mL of ethylacetate and at this time bigger portion of mono, di and tri-resveratrol glycolate was collected as fraction 2. Although fraction 2 still contained some impurities it had greater purity when compared to the original crude extract. The peak labeled with RMG indicates resveratrol mono-glycolate, RDG represents resveratrol di-glycolate and RTG represents Resveratrol tri-glycolate.

Example 2

Glycolic acid esters of resveratrol may also be prepared by reacting resveratrol (1 molar concentration) with NaH (6 molar) in a flow of argon gas in the presence of tetrahydrofuran, an aprotic solvent, at room temperature (25° C.) for 2-6 hours to form deprotonated resveratrol (A).
Step 1.

Then, glycolic acid is reacted with a mixture of dihydropyran (1.5 molar), p-Toluenesulfonic acid, pyridine, dimethylchloride, OC-RT for 3 to 12 hours to form glycolic acid where the terminal hydroxyl group has been protected with tetrahydropyran. The protected glycol acid is then reacted with a mixture of $SOCl_2$ (5 molar), dimethylformamide (cat.) and dimethylchloride under reflux conditions for 4-6 hours to form tetrahydropyran protected glycolic acyl chloride.
Step 2.

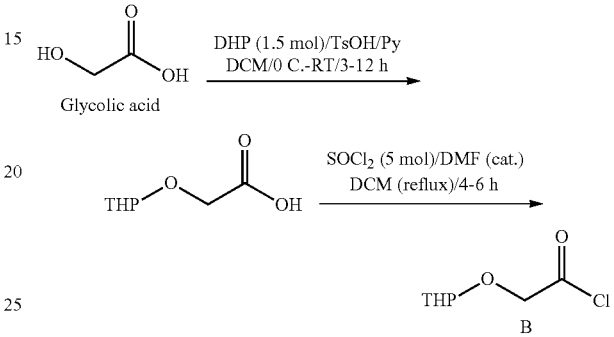

The deprotonated resveratrol (A) formed in step 1 is then reacted with the protected glycolic acyl chloride (B) formed in step 2, to form intermediate alpha hydroxyl protected resveratrol glycolate, which is then deprotected by reacting with 3.0 N HCl to form resveratrol glycolate which is in the form of a mixture of mono-, di-, and triester forms.
Step 3.

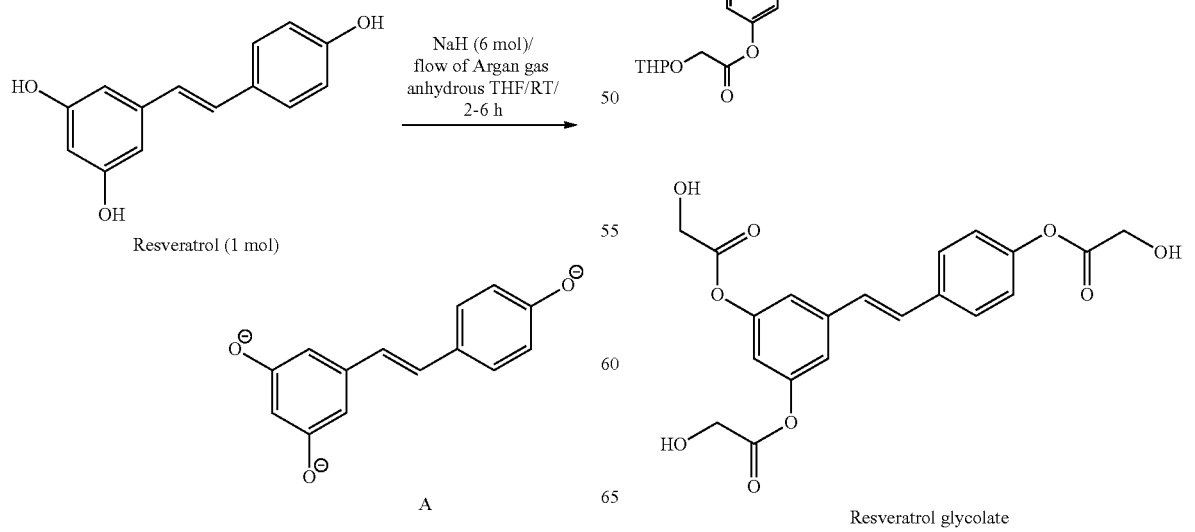

NaH: Sodium hydide
DHP: Dihydropyran
DMF: Dimethyl formamide
DCM: Dimethylchloride
TsOH: p-Toluenesulfonic acid
Trt: Trityl chloride
DIEA: N,N-Diisopropylethylamine
THF: Tertahydrofuran
TFA: Trifluoroacetic acid
EDT: 1,2-Ethanedithiol
MeOH: Methanol
NEt₃: Triethylamine

Example 3

Resveratrol glycolate is prepared by deprotonating resveratrol in the same manner as Step 1, above. Separately, glycolic acid is reacted with trityl chloride (1.5 molar) in N,N,-diisopropylethylamine (DIEA) to form glycolic acid where the hydroxyl group is protected with trityl chloride. The trityl chloride protected glycolic acid is then further reacted with $SOCl_2$ (5 molar), dimethylformamide (DMF), dimethylchloride (DMC) in reflux conditions for 4-6 hours to form trityl chloride protected glycolic acyl chloride (C).
Step 2

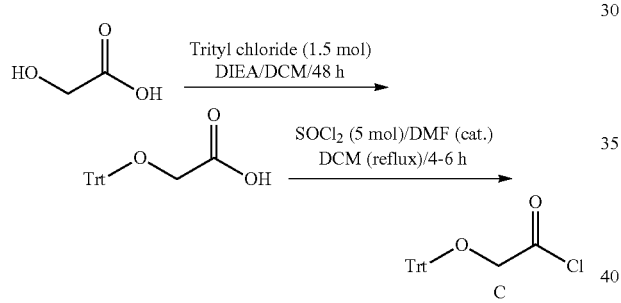

Then, 1 mole of (A) is mixed with 3 moles of (C) and reacted with triethylamine, tetrahydrofuran, at room temperature (25° C.) for 12-72 hours to form trityl chloride protected resveratrol glycolate which is thereafter treated with trifluoroacetic acid, 1,2-ethanediol, dimethylsulfide and dimethylchloride to remove the protecting groups to yield resveratrol glycolate.
Step 3.

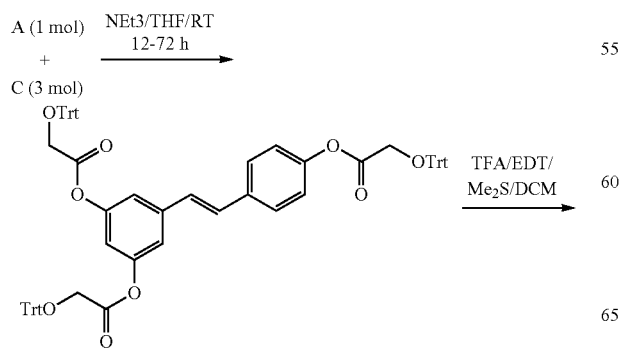

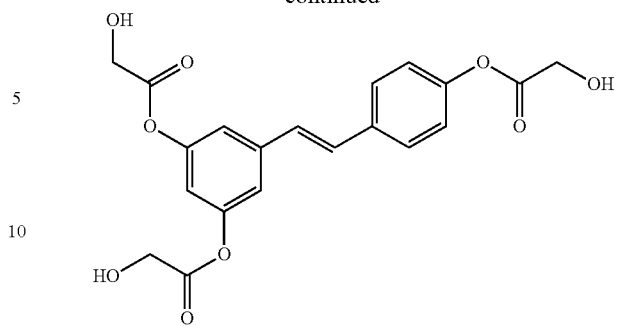

Resveratrol Glycolate

Example 4

Resveratrol glycolate is prepared by reacting the deprotonated resveratrol (A) obtained in Step 1 in Example 1 with a commercially available glycolic acyl chloride in the presents of triethylamine and tetrahydrofuran at room temperature for 12-72 hours to form resveratrol glycolate.

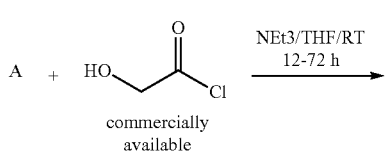

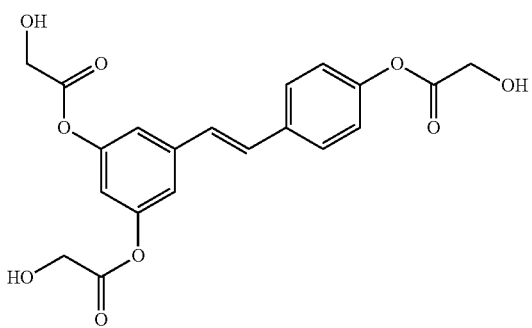

Resveratrol Glycolate

Example 5

Tartaric acid esters of resveratrol are prepared by deprotonating resveratrol in the same manner as set forth in Example 1, Step 1. Then L-tartaric acid is reacted with a mixture of acetic acid, acetic anhydride and pyridine at room temperature for 12-48 hours to form +-O—O'-Diacetyl-L-tartaric anhydride.

Step 2.

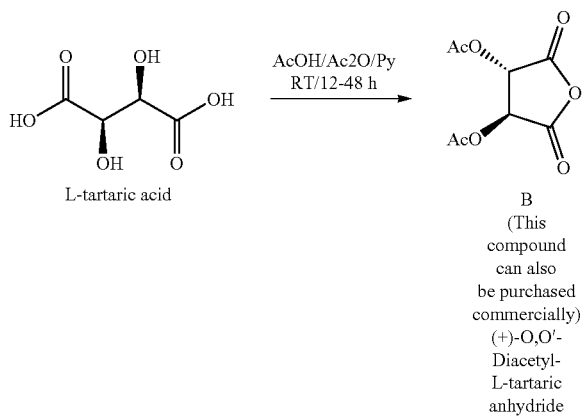 [SMILES: O=C(O)[C@H](O)[C@@H](O)C(=O)O ; CC(=O)O[C@@H]1C(=O)OC(=O)[C@H]1OC(C)=O]

L-tartaric acid

B
(This compound can also be purchased commercially)
(+)-O,O′-Diacetyl-L-tartaric anhydride Then 1 mole of (A) is reacted with 3 moles of (B) in the presence of trimethylamine and tetrahydrofuran at room temperature for 12-72 hours to form acyl protected tartaric acid which is then reacted with $K_2CO_3$ (10 molar), methanol, OC-RT for at least 1 hour, to form resveratrol tartrate.

Step 3.

A (1 mol)   NEt3/THF/RT
            12-72 h
+
B (3 mol)

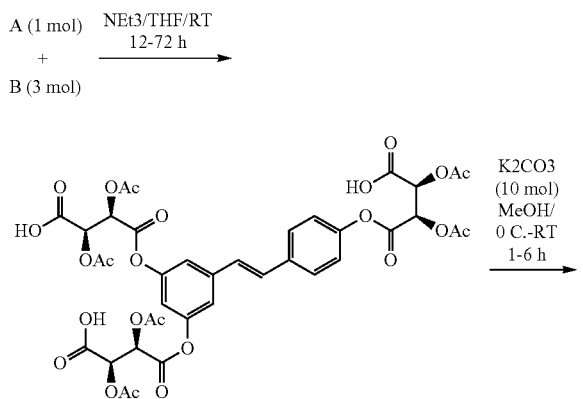

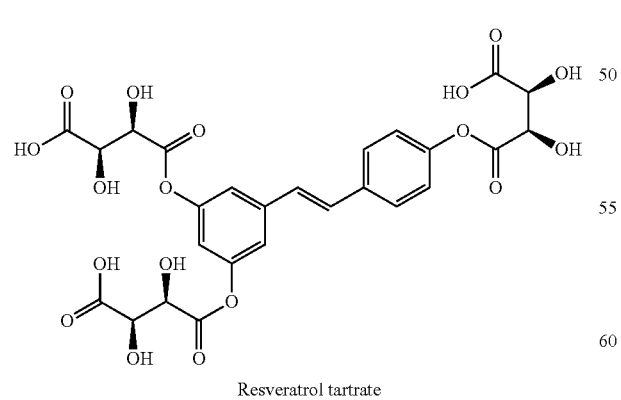

Resveratrol tartrate

The term "OC-RT" means zero degrees centigrade—room temperature.

Example 6

Emulsion compositions containing the resveratrol glycolate and tartrate are made as follows:

| Ingredient | Wt % #1 | Wt % #2 |
|---|---|---|
| Water | QS100 | QS100 |
| Resveratrol glycolate | 1.0 | — |
| Resveratrol tartrate | — | 0.5 |
| Glycerin | 10 | 10 |
| EDTA | 0.1 | 0.1 |
| PEG-60 hydrogenated castor oil | 0.1 | 0.1 |
| Phenoxyethanol | 0.5 | 0.5 |
| Carbopol | 0.3 | 0.5 |
| Behenyl alcohol | 0.5 | 0.5 |
| Glyceryl stearate SE | 4 | 8 |
| Tricaprylyl citrate | 5 | 5 |

The composition is prepared by combining the ingredients and mixing well to emulsify to a lotion.

Example 7

Anhydrous compositions are prepared as follows:

| Ingredient | Wt % #1 | Wt % #2 |
|---|---|---|
| Dimethicone/vinyl dimethicone crosspolymer/methyl trimethicone (10:90) | QS100 | QS100 |
| Resveratrol glycolate | 0.75 | — |
| Resveratrol tartrate | — | 2.0 |
| N-acetyl glucosamine | 0.5 | 0.5 |
| PEG-60 hydrogenated castor oil | 0.5 | 0.5 |
| *Simmondsia chinensis* (jojoba) seed oil | 20 | 20 |
| Glycerin | 10 | 10 |

The compositions are prepared by combining the ingredients and mixing well to form a serum.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

What is claimed is:

1. A compound of the formula:

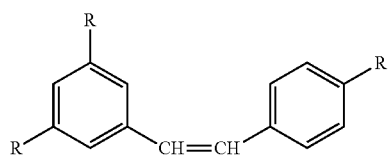

wherein each R is independently selected from:

—OH     (i)

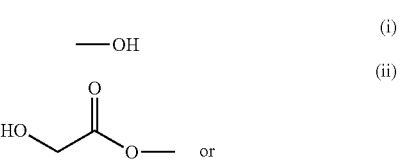     or     (ii)

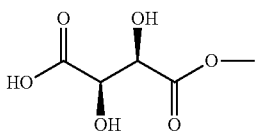

with the proviso that all R cannot simultaneously be —OH and all R cannot be simultaneously (ii).

2. The compound of claim 1 wherein two R are independently (i) and one R is (ii) and the compound is a resveratrol monoglycolate selected from the group consisting of 3-glycolate-5-4'-dihydroxystilbene; 5-glycolate-3,4'dihydroxystilbene; U and 4'-glycolate-3,5-dihydroxystilbene.

3. The compound of claim 1 wherein one R is (i) and two R are (ii) and the compound is a resveratrol diglycolate selected from the group consisting of 3,5-diglycolate-4'-hydroxystilbene; 3,4'-diglycolate-5-hydroxystilbene; and 3,4'-diglycolate-5-hydroxystilbene; 4'5-diglycolate-3-hydroxystilbene.

4. A composition comprising the compound of claim 1 in the form of a mixture wherein:
    two R are independently (i) and one R is (ii) and the compound is a resveratrol monoglycolate selected from the group consisting of 3-glycolate-5-4'-dihydroxystilbene; 5-glycolate-3,4'dihydroxystilbene; 4'-glycolate-3,5-dihydroxystilbene; and mixtures thereof; and
    one R is (i) and two R are (ii) and the compound is a resveratrol diglycolate selected from the group consisting of 3,5-diglycolate-4'-hydroxystilbene; 3,4'-diglycolate-5-hydroxystilbene; 3,4'-diglycolate-5-hydroxystilbene; 4'5-diglycolate-3-hydroxystilbene; and mixtures thereof; and.

5. The composition of claim 4 additionally comprising resveratrol.

6. The compound of claim 1 wherein two of R are (i) and one of R is (iii) and the compound is a resveratrol monotartrate selected from the group consisting of 3-tartrate-5-4'-dihydroxystilbene; 5-tartrate-3,4'dihydroxystilbene; and 4'-tartrate-3,5-dihydroxystilbene.

7. The compound of claim 1 wherein one of R is (i) and two of R are (iii) and the compound is a resveratrol ditartrate selected from the group consisting of 3,5-ditartrate-4'-hydroxystilbene; 3,4'-ditartrate-5-hydroxystilbene; 3,4'-ditartrate-5-hydroxystilbene; and 4'5-ditartrate-3-hydroxystilbene.

8. The compound of claim 1 wherein three of R are (iii) and the compound is resveratrol tritartrate or 3,5,4'-tritartrate stilbene.

9. A composition comprising the compound of claim 1 in the form of a mixture of where:
    two of R are (i) and one of R is (iii) and the compound is a resveratrol monotartrate selected from the group consisting of 3-tartrate-5-4'-dihydroxystilbene; 5-tartrate-3,4'dihydroxystilbene; 4'-tartrate-3,5-dihydroxystilbene; and mixtures thereof,
    one R is (i) and two of R are (iii) and the compound is resveratrol ditartrate and the compound is a resveratrol ditartrate selected from the group consisting of 3,5-ditartrate-4'-hydroxystilbene; 3,4'-ditartrate-5-hydroxystilbene; 3,4'-ditartrate-5-hydroxystilbene; 4'5-ditartrate-3-hydroxystilbene; and mixtures thereof,
    three R are (iii) and the compound is resveratrol tritartrate or 3,5,4'-tritartrate stilbene.

10. The composition of claim 9 additionally comprising resveratrol.

11. A method for synthesizing glycolic acid esters of resveratrol comprising the steps of:
    a) deprotonating resveratrol by reacting with a base,
    b) preparing alpha hydroxyl protected glycolic acid by:
        (i) reacting the alpha hydroxyl group of glycolic acid with compound having a protecting donor group to form a protected alpha hydroxy glycolic acid
        (ii) reacting (i) with halogen donor compound to form a reactive alpha hydroxyl acyl halide,
    c) reacting (a) and (b) to form alpha hydroxyl protected resveratrol glycolate; and
    d) deprotecting the protected alpha hydroxyl groups to form resveratrol glycolate.

12. A method for synthesizing tartaric acid esters of resveratrol comprising the steps of:
    (a) deprotonating resveratrol by reacting with a base,
    (b) preparing alpha hydroxyl protected tartaric acid anhydride by:
        (i) dehydrating tartaric acid to form a reactive tartaric acid anhydride,
        (ii) simultaneously reacting the alpha hydroxyl groups with a compound having a protecting donor group to form a protected tartaric acid anhydride,
    (c) reacting (a) and (b) to form alpha hydroxyl protected resveratrol tartrate; and
    (d) deprotecting the protected alpha hydroxyl groups to form resveratrol tartrate.

13. The composition of claim 4 in the form of a cream, serum, solution, dispersion, emulsion or lotion.

14. The composition of claim 9 in the form of a cream, serum, solution, dispersion, emulsion or lotion.

\* \* \* \* \*